(12) United States Patent
Mulla et al.

(10) Patent No.: US 10,731,219 B1
(45) Date of Patent: Aug. 4, 2020

(54) METHOD FOR PREVENTING PROGRESSION TO METABOLIC SYNDROME

(71) Applicant: DASMAN DIABETES INSTITUTE, Dasman (KW)

(72) Inventors: Fahd Al Mulla, Dasman (KW); Rasheeba Nizam, Dasman (KW); Ashraf Madhoun, Dasman (KW)

(73) Assignee: Dasman Diabetes Institute, Dasman (KW)

( * ) Notice: Subject to any disclaimer, the term of this patent is extended or adjusted under 35 U.S.C. 154(b) by 0 days.

(21) Appl. No.: 16/576,266

(22) Filed: Sep. 19, 2019

(51) Int. Cl.
*C07H 21/04* (2006.01)
*C12Q 1/68* (2018.01)
*C12Q 1/6883* (2018.01)

(52) U.S. Cl.
CPC ...... *C12Q 1/6883* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

2006/0154249 A1    7/2006  Salonen
2015/0352064 A1   12/2015  Bitar et al.

FOREIGN PATENT DOCUMENTS

RU    2492485 C1    9/2013
WO  2009055596 A2    4/2009
WO  2014006231 A1    1/2014

OTHER PUBLICATIONS

Baudrand et al. (Metabolism Clincial and Experimental, vol. 64, pp. 1674-1681, 2015). (Year: 2015).*
Mora-Garcia et al. (Metabolic Syndrome and related disorders, vol. 16, pp. 453-463, 2018). (Year: 2018).*
Nizam et al. (Frontiers in Genetics, vol. 9, Article 689, Dec. 2018). (Year: 2018).*
Baudrand, R. et al., "A prevalent caveolin-1 gene variant is associated with the metabolic syndrome in Caucasians and Hispanics," Metabolism 64(11): pp. 1674-1681 (2015).
Grilo, A. et al., "Genetic analysis of CAV1 gene in hypertension and metabolic syndrome," Thromb. Haemost. 95: pp. 696-701, (2006).
Iguchi, K. et al., "Inhibition of Caveolin-1 Expression by Incadronate in PC-3 Prostate Cells," Anticancer Research 26: pp. 2977-2982 (2006).

(Continued)

*Primary Examiner* — Jeanine A Goldberg
(74) *Attorney, Agent, or Firm* — Richard C. Litman; Nath, Goldberg & Meyer

(57) ABSTRACT

The method for preventing progression to metabolic syndrome includes determining whether a subject possesses at least one allele of the caveolin-1 rs1997623 C to A SNP, and providing an intervention to prevent progression to metabolic syndrome, including modifications of diet and exercise, administration of one or more pharmaceutical compounds, or a combination thereof. The method may be useful to reduce the risk of developing complications associated with MetS, such as heart disease, stroke, or diabetes. The method may include monitoring additional metabolic risk factors. The pharmaceutical compound may be a pharmaceutical capable of inhibiting the expression of caveolin-1.

5 Claims, 4 Drawing Sheets

Specification includes a Sequence Listing.

(56) References Cited

OTHER PUBLICATIONS

Le Saux, C. J. et al., "Down-regulation of Caveolin-1, an Inhibitor of Transforming Growth Factor-B Signaling, in Acute Allergen-induced Airway Remodeling," J. of Biological Chem. 283(9): pp. 5760-5768 (2008).
Guruswamy, S., "Caveolin-1 as a target for colon cancer inhibition by lovastatin and celecoxib," AACR Annual Meeting, Los Angeles, CA (2007).
Shimato, S. et al., "Inhibition of Caveolin-1 Restores Myeloid Cell Function in Human Glioblastoma," PLOS One 8 (10) (2013).
Pedram, P. "Nutritional, hormonal and genetic factors in the development of overeating tendency toward food addiction," Faculty of Medicine, Memorial University of Newfoundland (2017).

* cited by examiner

METHOD FOR PREVENTING PROGRESSION TO METABOLIC SYNDROME

The Applicants hereby incorporate by reference the sequence listing contained in the ASCII text filed titled 33024_00_sequence_listing_ST25.txt, created Jul. 16, 2019, and having 1 KB of data.

BACKGROUND

1. Field

The disclosure of the present patent application relates to the medical sciences, and particularly to a non-invasive method for determining a subject's risk of developing metabolic syndrome and intervening to prevent progression to metabolic syndrome.

2. Description of the Related Art

Metabolic syndrome (MetS) affects an estimated 1 in 5 Americans. MetS is a condition characterized by the presence of a specific group of risk factors increasing a subject's risk of developing further diseases. The risk factors include elevated resting blood pressure, elevated fasting blood sugar, high triglyceride levels, low HDL cholesterol, and excess body fat around the waist. Those with MetS have an increased risk of developing diabetes, damage to the lining of the coronary or other arteries leading to heart disease, high blood pressure, stroke, increased triglyceride levels, blood clots, and fatty liver disease. Although the precise causes of metabolic syndrome are unknown, risk factors include abdominal obesity and insulin resistance. Family studies have shown that metabolic syndrome is heritable, indicating that genetic factors play a role in individual susceptibility to metabolic syndrome.

However, the primary approach to diagnosing MetS depends upon assessing the risk factors used to define the condition. These diagnostics require invasive procedures such as blood draws. These diagnostics are further limited in that they do not predict which patients are at a particularly increased risk of developing MetS risk factors in the future.

Thus, a method for predicting and preventing progression to metabolic syndrome solving the aforementioned problems is desired.

SUMMARY

The present subject matter relates to a method for preventing progression to metabolic syndrome, including detecting increased risk of developing metabolic syndrome in a subject and intervening to prevent development of metabolic syndrome. In an embodiment, the intervention may include administering a pharmaceutical composition to the subject, prescribing a modified diet or exercise regime for the subject, or a combination thereof. In an embodiment, a subject's risk of developing metabolic disease may be determined by identifying the subject's genotype at a specific SNP in the Caveolin 1 gene (CAV1). In an embodiment, the specific SNP in CAV1 is rs1997623, and the presence of at least one "A" nucleotide at the CAV1 rs1997623 SNP is indicative of an increased risk of developing metabolic syndrome.

In an embodiment, the subject may be a child. In a further embodiment, the subject may be of Arab descent.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
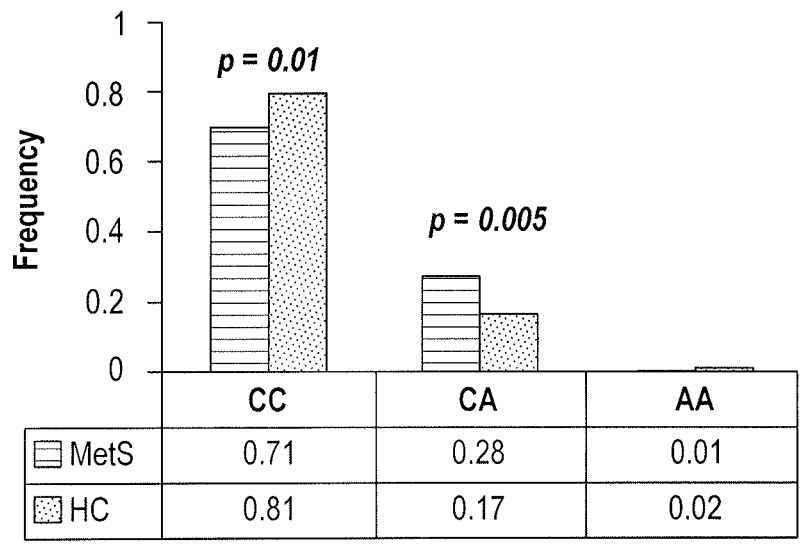
FIG. 1 depicts a bar graph plotting the frequency of the Caveolin-1 rs1997623 SNP in children having metabolic syndrome against the frequency of the Caveolin-1 rs1997623 SNP in healthy children.

The present subject matter relates to a method for preventing progression to metabolic syndrome (MetS), including detecting increased risk of developing MetS in a subject and intervening to prevent development of MetS in a subject having a detected increased risk of developing MetS. In an embodiment, the intervention may include administering a pharmaceutical composition to the subject, prescribing a modified diet for the subject, prescribing a modified exercise regime for the subject, or a combination thereof. In an embodiment, a subject's risk of developing metabolic disease may be determined by identifying the subject's genotype at a specific SNP in the Caveolin 1 gene (CAV1). In an embodiment, the specific SNP in CAV1 is rs1997623, and the presence of at least one "A" nucleotide at this SNP is indicative of an increased risk of developing MetS.

As used herein, "metabolic syndrome" is a collection of health risks and conditions that may increase the chance of developing, and relate to, heart disease, stroke, and diabetes.

These health risks and conditions include increased blood pressure, high blood sugar, excess body fat, particularly excess body fat around the waist, and abnormal cholesterol or triglyceride levels. In order to be diagnosed with metabolic syndrome, a subject must generally exceed specific parameters for three or more of the health risks and conditions.

As used herein, "nucleic acid" means a polynucleotide such as a single or double-stranded DNA or RNA molecule, including, for example, genomic DNA, cDNA, and mRNA. The term nucleic acid includes nucleic acid molecules of both natural and synthetic origin, as well as molecules of linear, circular, or branched configuration representing either sense or antisense strands, or both, of a native nucleic acid molecule.

As used herein, "subject" means a mammal, such as a human being.

As used herein, "biological sample" means any biological material from which nucleic acid molecules can be prepared. Non-limiting examples of suitable biological samples useful herein include whole blood, plasma, saliva, cheek swab, or other bodily fluids or tissues that contain nucleic acids.

As used herein, "risk variant" corresponds to genetic variants that are associated with an increased likelihood of an individual developing metabolic syndrome or associated conditions, such as insulin resistance, fatty liver, heart disease, cardiovascular disease, and obesity, as compared to a healthy individual.

As used herein, "SNP" corresponds to a single nucleotide polymorphism, or a genetic variation in a single nucleotide, such as a replacement of cytosine (C) or guanine (G) with thymine (T) or adenine (A) at a specific location in the genome. SNPs are frequently used as biological markers, as particular SNPs may associate with genes that play a role in particular diseases. More rarely, a SNP may itself play a role in a disease by affecting a particular gene's expression or function.

Many methods are available for detection of one or more risk variants of a SNP, including sequencing methods, re-sequencing methods, amplification methods, and hybridization methods. Analysis of nucleic acids in a biological sample from an individual, whether amplified or not, may be performed using any of these methods. Exemplary methods include but are not limited to polymerase chain reaction (PCR), restriction fragment length polymorphism analysis (RFLP), reverse-transcription PCR (RT-PCR), isothermal amplification, 5' fluorescence nuclease assay (e.g. TAQMAN assay), molecular beacon assays, heteroduplex mobility assays (HMA), single strand conformational polymorphism (SSCP), and denaturing gradient gel electrophoresis (DGGE). One of ordinary skill in the art would understand that any known method of amplification of a nucleotide could be incorporated into a method to detect one or more risk variants of a SNP. One of ordinary skill in the art would further understand that these methods of amplification of a nucleotide could use DNA, RNA, or a combination of the two.

These assays may be multiplexed, meaning two or more reactions may be conducted simultaneously in the same physical location, such as in the same tube or on the same substrate, such as a biochip, ensuring that the reaction products of the multiplexed reactions can be distinguished. For example, TAQMAN or molecular beacon assays can be multiplexed by use of any by monitoring of accumulation or depletion of two different fluorochromes corresponding to different sequence specific probes.

As used herein, "PCR" is any method involving the amplification of a nucleotide sequence based upon complementary primer binding to a target sequence. One of ordinary skill in the art will understand that PCR may be employed as part of many techniques for identifying a SNP risk variant, including but not limited to Tetra-primer amplification refractory mutation system PCR (ARMS-PCR). In ARMS-PCR, primers are employed whose 3' ends encompass the SNP location, with each primer encoding a different allele at the SNP location. The primers are also designed to produce different length amplification fragments, thus allowing discrimination of the SNP genotype based upon the length of the amplified fragments.

As used herein, "RFLP" is any method for distinguishing genetic polymorphisms using a restriction enzyme, which is an endonuclease that catalyzes the degradation of nucleic acid and recognizes a specific base sequence, generally a palindrome or inverted repeat. One of ordinary skill in the art would understand that the use of RFLP analysis depends upon an enzyme that can differentiate two alleles at a polymorphic site.

As used herein, "RT-PCR" is any method involving the amplification of a RNA sequence using a reverse transcriptase to produce a cDNA sequence, followed by amplification of a nucleotide sequence based upon complementary primer binding to a target sequence. One of ordinary skill in the art will understand that RT-PCR may be employed as part of many techniques for identifying a SNP risk variant.

As used herein, "isothermal amplification" is any method involving amplification of a nucleotide sequence based upon complementary primer binding to a target sequence performed at a constant temperature. One example of an isothermal amplification method is loop-mediated isothermal amplification (LAMP). Generally, LAMP is used to amplify from a DNA sequence and is performed using multiple primer sets and a polymerase with a high strand displacement activity. Another example of an isothermal amplification method is nucleic acid sequence based amplification (NASBA). Generally, NASBA is used to amplify from a RNA sequence and is performed using a reverse transcriptase, an RNAse, and a RNA polymerase.

As used herein, a "5' fluorescence nuclease assay" is any method using a target allele specific probe bearing a 5' fluorescent dye label. In general, when the allele specific probe is used to amplify the target sequence, the 5'-nuclease activity of the polymerase cleaves the 5' fluorescent dye label off of the probe, changing the molecular weight of the fluorescent dye molecule and therefore changing the fluorescence polarization. This change in fluorescence polarization may be detected, thereby confirming the presence of the target allele.

As used herein, "hybridization methods" mean methods relying on the use of a labeled oligonucleotide probe having a sequence complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used to selectively amplify, for example, a non-disease-predisposing allele by using an allele-specific oligonucleotide primer that is complementary to the nucleotide sequence of the non-disease-predisposing allele but which has one or more mismatches as compared to other alleles. One of ordinary skill in the art will understand that the one or more nucleotide mismatches that distinguish between the disease-predisposing allele (or the non-disease promoting allele) and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer. Non-limiting examples of hybridization methods useful herein include molecular beacon assays.

As used herein, a "HMA assay" is useful for detecting the presence of a polymorphic sequence since a DNA duplex carrying a mismatch has reduced mobility in a polyacrylamide gel compared to the mobility of a perfectly base-paired duplex.

As used herein, "SSCP" can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

As used herein, "DGGE" can be used to detect SNPs by electrophoresis of double-stranded DNA in a gel containing an increasing concentration of denaturant. The double-stranded DNA fragments containing mismatched alleles will have segments that will likely melt more rapidly, causing such fragments to migrate at a different rate compared to perfectly complementary sequences.

When implementing methods for detection of one or more SNPs, an array may be used to perform a high-throughput assay. The array generally comprises one or more reagents, such as nucleic acid primers and/or probes, for identifying in a nucleic acid sample from a subject the occurrence of an allelic variation corresponding to one or more SNPs. These reagents may be immobilized onto a substrate in a spatially addressable manner, such that each reagent is located at a different, identifiable, position on the array. The substrate may include multi-welled plates, ceramic chips, or beads. In a non-limiting example, the substrate may be a 96 well dish, with each well constituting a reaction chamber within which separate reactions comprising identified constituents may be performed. The reaction constituents may include primers for amplifying DNA or probes for binding specific sequences and reaction reagents. The reagents may be in any suitable form, including but not limited to: in solution, dried, lyophilized, or glassified. In a further non-limiting example, the array may include two or more sets of beads, with each bead having an identifiable marker, such as a quantum dot or fluorescent tag, so that the beads may be individually identified using, for example, a flow cytometer. Non-limiting examples of array technologies that may be employed include: the Affymetrix GeneChip® Array or the GenChip® CustomSeq® Resequencing Arrays. Informatics and/or statistical software or other computer-implemented processes for analyzing array data and/or identifying genetic risk factors from data obtained from a patient sample are well known in the art and would be readily understood by the ordinarily skilled artisan.

Other molecular methods useful for determining the presence or absence of a SNP known in the art may also be used when performing the method for preventing progression to metabolic syndrome.

In an embodiment, the subject may be a child. In a further embodiment, the subject may be of Arab descent.

In an embodiment, the method for preventing progression to metabolic syndrome may include identifying subjects possessing a genetic risk variant. The genetic risk variant may be the presence of one or more "A" alleles at the CAV1 rs1997623 locus. The presence of a risk variant may be identified by collecting a biological sample from a subject and detecting the presence of the risk variant using PCR, RFLP, RT-PCR, isothermal amplification, 5' fluorescence nuclease assay (e.g. TAQMAN assay), molecular beacon assays, HMA, SSCP, DGGE, or the like.

In an embodiment, the biological sample may be collected from the subject in a non-invasive manner. In a non-limiting example, the biological sample may be saliva.

In an embodiment, a subject identified as possessing the risk variant may then receive one or more interventions to prevent progression to MetS. Possible interventions include but are not limited to pharmaceutical treatments, diet, exercise, or a combination thereof. In a non-limiting example, a subject found to possess the CAV1 rs1997623 SNP, and thus to be at increased risk of developing MetS, may be prescribed at least 30 minutes of exercise a day, or a diet that is low in fat and refined, processed sugars, or a combination thereof. In a further non-limiting example a subject found to be at increased risk of developing MetS may be prescribed any appropriate dietary restriction, including but not limited to restricted calorie, low fat, low carbohydrate, flexitarian, vegan, and raw food diets.

In a further non-limiting example, a subject found to possess the CAV1 rs1997623 SNP, and thus to be at increased risk of developing MetS, may receive intervention via a pharmaceutical treatment. Potential pharmaceuticals for administration to a subject at increased risk of developing MetS include compositions capable of inhibiting the expression or activity of CAV1, including but not limited to 18α-Glycyrrhetinic acid, Incadronate (disodium cycloleptylaminomethylene diphosphonate), Interleukin-4, a combination of Celecoxib and Lovastatin, or an anti-CAV1 siRNA, or a combination thereof.

In an embodiment, intervention to prevent the progression of MetS may also be used to prevent the development of one or more comorbidities associated with obesity, including but not limited to hypertension, diabetes, and cardiovascular disease.

In an embodiment, the CAV1 rs1997623 risk variant may also be used to predict decreased salivary concentration of good cholesterol in a subject.

In an embodiment, the identification of a subject as possessing the CAV1 rs1997623 risk variant sequence may be one of multiple predictive factors used to predict MetS. Further factors considered in predicting MetS may include height, weight, body mass index (BMI), heart rate, saliva flow rate, waist circumference, systolic blood pressure, diastolic blood pressure, saliva glucose concentration, saliva high density lipoprotein cholesterol concentration (HDLC), and the like. Bounds may then be determined for each of these predictive factors, beyond which the subject is considered at increased risk for developing MetS. These bounds may be readily determined by one of ordinary skill in the art, based upon their understanding of what constitutes an increased risk for developing MetS for a particular risk factor. A biological sample and relevant physical readings may be collected from a subject, and the number of factors exceeding the set bounds for each factor may be totaled, to determine the subject's risk score. Subjects may then be classified based in their risk score into categories, including those not at increased risk for developing MetS (non-MetS), those at an intermediate risk of developing MetS (Int-MetS), and those at significant risk of developing or already experiencing MetS (MetS). In all instances, the presence of the CAV1 rs1997623 risk variant must be one of the factors measured.

In a non-limiting example, a group of four factors may be selected, such as the presence of the CAV1 rs1997623 risk variant, systolic blood pressure, diastolic blood pressure, and waist circumference. The bounds may be the presence of the CAV1 rs1997623 SNP, a systolic blood pressure above 130, a diastolic blood pressure above 85, and a waist circumference above the 90$^{th}$ percentile. Subjects having a risk score of 4 may be classified as MetS, subjects having a risk score of 2 or 3 may be classified as Int-MetS, and subjects having a risk score of 0 or 1 may be classified as non-MetS. The specific risk factors, in addition to the CAV1 rs1997623 risk variant, as well as the bounds thereof, may be selected generally or may be separately selected for each specific subject studied.

In a further embodiment, subjects may first be screened for the presence of the CAV1 rs1997623 risk variant using a non-invasive screening method (such as collecting saliva). Subjects that test positive for the presence of the CAV1 rs1997623 risk variant may then be screened for further factors to determine whether the subjects currently have MetS or are at an increased risk of developing MetS. Further factors considered in predicting MetS may include height, weight, body mass index (BMI), heart rate, saliva flow rate, waist circumference, systolic blood pressure, diastolic blood pressure, saliva glucose concentration, saliva high density lipoprotein cholesterol concentration (HDLC), and the like. Bounds may then be determined for each of these predictive factors, beyond which the subject is considered at increased risk for developing MetS. These bounds may be readily determined by one of ordinary skill in the art, based upon their understanding of what constitutes an increased risk for developing MetS for a particular risk factor. A biological sample and relevant physical readings may be collected from a subject, and the number of factors exceeding the set bounds for each factor may be totaled, to determine the subject's risk score. Subjects may then be classified based in their risk score into categories, including those at an increased risk of developing MetS (Int-MetS), and those already experiencing MetS (MetS).

A kit used to carry out the method for preventing progression to metabolic syndrome may contain various components needed for carrying out the method packaged in separate containers and/or vials and including instructions for carrying out the method. In a non-limiting example, some or all of the various components and other ingredients needed to detect the presence of the CAV1 rs1997623 risk variant, such as buffers, primers, enzymes, control samples or standards and the like can be packaged separately but provided for use in the same container. Instructions for carrying out the method can be included inside the container, as a separate insert, or as a label on the container and/or on the separate packaging. The kit may also contain the necessary software (or instructions to download the same) needed to interpret the results obtained with the kit, or for utilizing the results in a particular high-throughput assay selected for carrying out the method.

The following examples illustrate the present teachings.

Example I

Population Study

The inventors identified the CAV1 rs1997623 SNP as a population-specific risk variant from an in-house exome database including data from 156 adult Arabs. They then conducted a candidate gene study to evaluate the risk association of the CAV1 rs1997623 SNP with indicators of metabolic complications associated with childhood obesity. Saliva samples were used as specimens to analyze the association of the candidate variant with metabolic complications related to obesity. A cohort of Kuwaiti school children were recruited from all six Kuwaiti governorates covering 138 schools in 2011. A total of 8317 children were enrolled in the original study. On average, 23 schools were visited per governorate (range 13-31 schools per governorate) and an average of 46 children per school participated. A subset (1313 participants) was chosen by random sampling, representing 3% of the target population. Each participant provided a sample of saliva (3 ml) after an overnight fast. The samples were subjected to biochemical analysis to determine salivary glucose, salivary HDLC, and to isolate DNA. Routine information was collected from each participant, including their height, weight, blood pressure, and waist circumference (WC). Fitness was assessed by measuring heart rate elevation following 3 minutes of standard exercise. The resulting data are summarized in Table 1. P-values were calculated using the one-way ANOVA test.

TABLE 1

Characteristics of Study Subjects Based on the Scoring System for Metabolic Syndrome (MetS)

|  | All | MetS (≥3) | Int. (1 or 2) | Non-MetS (0) | p Value |
| --- | --- | --- | --- | --- | --- |
| Number (n) | 1313 | 246 | 834 | 233 |  |
| Gender (M/F) | 472/841 | 105/141 | 293/541 | 74/159 | 0.024 |
| Age (years) | 12.08 ± 0.64 | 12.04 ± 0.62 | 12.08 ± 0.65 | 12.11 ± 0.61 | 0.411 |
| Body Weight (kg) | 53.25 ± 16.70 | 70.24 ± 15.44 | 51.24 ± 15.14 | 42.60 ± 8.39 | <0.001 |
| Waist Circ. (cm) | 80.16 ± 14.56 | 91.85 ± 14.099 | 78.84 ± 13.95 | 72.59 ± 9.14 | <0.001 |
| BMI (kg/m$^2$) | 22.91 ± 5.94 | 29.26 ± 5.13 | 22.17 ± 5.35 | 18.87 ± 2.79 | <0.001 |
| Obesity % | 34.3 | 91.9 | 26.8 | 0 |  |
| Saliva HDLC (mg/dL) | 0.95 ± 1.50 | 0.61 ± 1.20 | 1.01 ± 1.53 | 2.11 ± 1.95 | <0.001 |
| Saliva Glucose (mg/dL) | 0.16 ± 0.34 | 0.26 ± 0.53 | 0.15 ± 0.31 | 0.062 ± 0.05 | <0.001 |
| DBP (mmHg) | 78.93 ± 13.96 | 90.57 ± 11.13 | 78.15 ± 13.45 | 69.39 ± 8.98 | <0.001 |
| SBP (mmHg) | 116.37 ± 16.74 | 131.02 ± 13.35 | 115.27 ± 15.7 | 104.87 ± 12.04 | <0.001 |
| Fitness (beats/min) | 21.33 ± 14.85 | 25.75 ± 13.69 | 23.56 ± 13.66 | 21.84 ± 13.96 | 0.012 |

TABLE 1-continued

Characteristics of Study Subjects Based on
the Scoring System for Metabolic Syndrome (MetS)

|  | All | MetS (≥3) | Int. (1 or 2) | Non-MetS (0) | p Value |
|---|---|---|---|---|---|
| Saliva flow rate (ml/hr) | 26.40 ± 45.12 | 27.30 ± 18.67 | 27.07 ± 51.29 | 22.96 ± 15.61 | 0.41 |
| Heart rate (beats/min) | 91.14 ± 25.90 | 93.38 ± 15.25 | 89.88 ± 13.89 | 93.26 ± 53.39 | 0.065 |
| Sleep (hours/week) | 8.96 ± 3.10 | 8.70 ± 3.21 | 9.00 ± 3.09 | 9.05 ± 3.05 | 0.421 |

HDLC and glucose were measured using fluorescent spectroscopic analysis (Infinate® 200 Pro, Tecan, Grondig, Austria) using commercially available kits (BioVision, Mountain View Calif.).

Each participant was scored for MetS depending upon the tested risk factors. Specifically, participants were considered to have MetS if they had at least three of four primary risk factors. The primary risk factors assessed were waist circumference ≥the $90^{th}$ percentile, a systolic blood pressure (SBP)≥130 or a diastolic blood pressure (DBP)≥85, a reduced salivary HDLC<0.6 mg/dL (the equivalent of an extrapolated blood concentration of 40 mg/dL) and an elevated salivary glucose≥1.13 mg/dL (the equivalent of an extrapolated blood concentration of 100 mg/dL). Participants were categorized as non-MetS if they had none of the four primary risk factors. Participants having 1 or 2 of the primary risk factors were categorized as "Int-MetS" or an intermediate risk group.

Of the participants tested, 246 children were classified as MetS, of which 99.1% were classified as obese based upon waist circumference. A total of 233 children were classified as non-MetS, while 834 children were classified as Int-MetS. The Int-MetS children included 26.8% of participants that were categorized as obese, 35.5% of those with elevated blood pressure, and 61.5% of those with low HDLC.

DNA was extracted from the saliva samples using the QIAamp® DNA extraction kit from Qiagen (Hilden, Germany) according to the manufacturer's instructions. CAV1 rs197623 SNP genotyping was carried out using allele specific probes and a pair of gene specific primers on an ABI 75000 real-time PCR system (Applied Biosystems). Genotyping results were confirmed by direct sequencing of the PCR products for selected cases. Genetic association analysis was conducted using the Statistical Package for the Social Sciences, SPSS version 25.0'. The genotyping results are summarized in Table 2. P-values were calculated using the Chi-square test and the overall distribution of rs1997623 across the three studied groups showed a significant association with $X^2$=11.64, p=0.02.

TABLE 2

Allele and Genotypic Distribution of the CAV1
rs1997623 SNP Based on Metabolic Syndrome Risk Score

| rs1997623/Allele | MetS (≥3) | Intermediate (1 or 2) | Non-MetS (0) |
|---|---|---|---|
| Allele C | 413 (0.85) | 1391 (0.85) | 412 (0.90) |
| Allele A | 73 (0.15) | 255 (0.15) | 44 (0.10) |
| p-value | 0.01 | 0.002 | |
| OR (95% CI) | 1.66 (1.11-2.46) | 1.71 (1.22-2.40) | |

| rs1997623/Genotype | MetS (≥3) | Intermediate (1 or 2) | Non-MetS (0) |
|---|---|---|---|
| Homozygous WT CC | 172 (0.71) | 587 (0.71) | 186 (0.81) |
| p-value | 0.01 | 0.004 | |
| OR (95% CI) | 0.57 (0.37-0.88) | 0.59 (0.40-0.84) | |
| Heterozygous CA | 69 (0.28) | 217 (0.26) | 40 (0.17) |
| p-value | 0.005 | 0.005 | |
| OR (95% CI) | 1.88 (1.21-2.93) | 1.70 (1.17-2.47) | |
| Homozygous Mutant AA | 2 (0.01) | 19 (0.02) | 4 (0.02) |
| p-value | 0.44 | 0.600 | |
| OR (95% CI) | 0.45 (0.085-2.59) | 1.34 (0.45-3.96) | |
| Complied (CA + AA) vs. CC | 71 (0.29)/172 (0.71) | 236 (0.29)/587 (0.71) | 44 (0.19)/186 (0.81) |
| p-value | 0.01 | 0.004 | |
| OR (95% CI) | 1.75 (1.13-2.68) | 1.7 (1.18-2.44) | |

Analysis of the genotyping results revealed a significant association between the CAV1 rs1997623 CA/AA genotype and MetS. Further, a comparison of non-MetS children with MetS children revealed significantly increased measures of body weight (p=0.002), BMI (p=0.001), WC (p=0.004), DBP (p=0.001), and SBP (p=0.02) in children carrying mutant genotypes at CAV1 rs1997623 when compared with children with the wild type (CC) genotype (See FIGS. 6B-6F).

Figure 2:
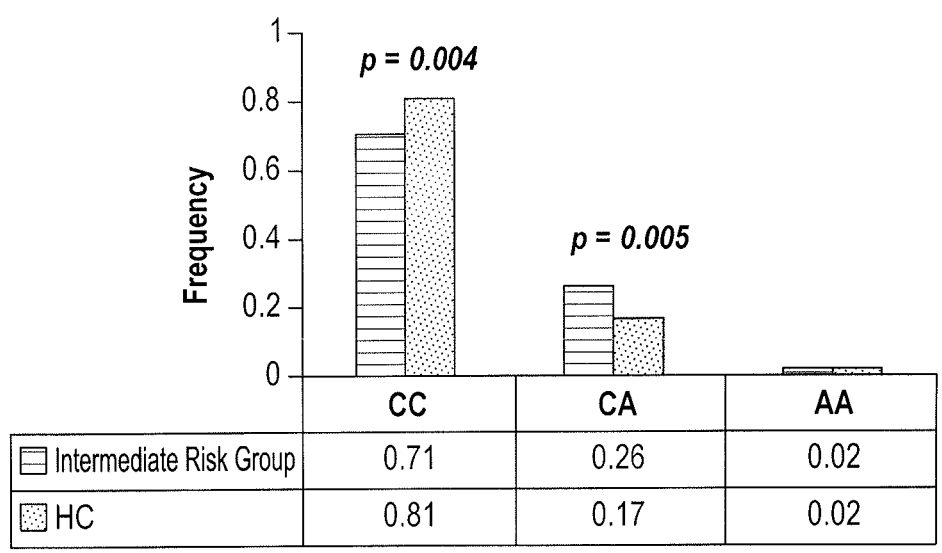
FIG. 2 depicts a bar graph plotting the frequency of the Caveolin-1 rs1997623 SNP in children categorized as at intermediate risk of developing metabolic syndrome against the frequency of the Caveolin-1 rs1997623 SNP in healthy children.
Figure 3:
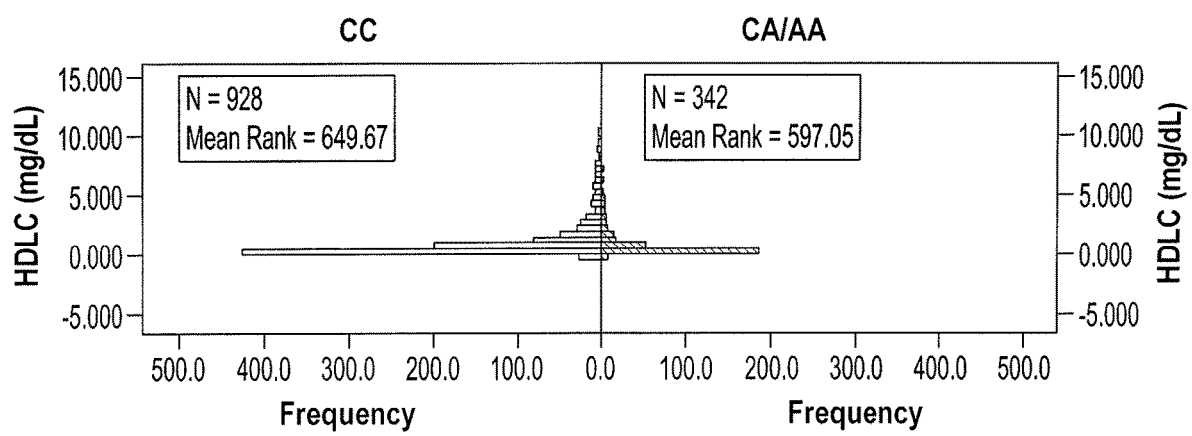
FIG. 3 depicts a graph of the high density lipoprotein cholesterol levels of children carrying the mutant CA or AA genotype at the Caveolin-1 rs199762 SNP locus and the high density lipoprotein cholesterol levels of children having the wildtype CC genotype at the Caveolin-1 rs199762 SNP locus.

As shown in FIG. 1, the heterozygous CAV1 rs1997623 CA genotype showed a significant association with MetS compared to the non-MetS group (p=0.005, Odds Ratio (OR)=1.88 at 95% Confidence Interval (CI) 1.21-2.93). As shown in FIG. 2, there was a significant association of the CAV1 rs1997623 A-allele (p=0.002, OR=1.71 at 95% CI 1.22-2.40) and CA genotype (p=0.005, OR=1.70 at 95% CI 1.17-2.47) with the intermediate metabolic group compared with the non-MetS group. The overall distribution of genotype frequencies (CA+AA versus CC) also revealed significant association of the CAV1 rs1997623 SNP with MetS (p=0.01, OR=1.75 at 95% CI, 1.13-2.68) and with the intermediate metabolic group (p=0.004, OR=1.7 at 95% CI 1.18-2.44).

A logistical regression analysis was performed to determine the effects of CAV1 rs1997623, age, and gender on the likelihood of children having MetS. The analysis revealed that gender contributed significantly with a p=0.006. Compared to the wildtype CC genotype, children with the CA genotype had an increased susceptibility to MetS with a p=0.004 and adjusted odds ratio (AOR) of 1.938 at 95% CI 1.24-3.029. To further analyze the overall effect of the CAV1 rs1997623 variant, data from children carrying the mutant allele were combined (CA and AA genotypes). Compared to wildtype (CC genotype), children carrying the mutant allele showed increased susceptibility to MetS with a p=0.008 and AOR of 1.806 at 95% CI 1.170-2.789. The results of the logistic regression analysis are summarized in Table 3. P-values were adjusted for age and gender.

TABLE 3

Logistic Regression Analysis of the rs1997623 Variant in a Group of Subjects With and Without Metabolic Syndrome

| MetS (≥3)/Non-MetS (0) | p-value | AOR | 95% CI |
|---|---|---|---|
| Sex/Male Reference | | | |
| Female | 0.006 | 0.582 | 0.397-0.853 |
| Age | 0.193 | 0.819 | 0.606-1.106 |
| rs1997623/CC Reference | | | |
| CA Genotype | 0.004 | 1.938 | 1.240-3.029 |
| AA Genotype | 0.467 | 0.527 | 0.094-2.967 |
| CA + AA Genotypes | 0.008 | 1.806 | 1.170-2.789 |

TABLE 4

Allele and Genotypic Distribution of the CAV1 rs1997623 SNP in low HDLC Subjects Compared to the Control Group

| rs1997623 | LHDLC | NHDLC | p-value | OR | 95% CI |
|---|---|---|---|---|---|
| C | 1216 (0.84) | 1000 (87) | 0.01 | 1.33 | 1.05-1.658 |
| A | 232 (0.16) | 144 (0.13) | | | |

TABLE 4-continued

Allele and Genotypic Distribution of the CAV1 rs1997623 SNP in low HDLC Subjects Compared to the Control Group

| rs1997623 | LHDLC (724) | NHDLC (572) | p-value | OR | 95% CI |
|---|---|---|---|---|---|
| CC | 504 (0.70) | 441 (0.77) | 0.002 | 0.68 | 0.53-0.88 |
| CA | 208 (0.29) | 118 (0.21) | 0.0008 | 1.55 | 1.197-2.008 |
| AA | 12 (0.02) | 13 (0.02) | 0.42 | 0.725 | 0.33-1.601 |

TABLE 5

Logistic Regression Analysis of the rs1997623 Variant in a Group of Subjects With Low HDLC and Normal HDLC

| LHDLC/NHDLC | p-value | AOR | 95% CI |
|---|---|---|---|
| Sex/Male Reference | | | |
| Female | 0.017 | 0.754 | 0.598-0.950 |
| Age | 0.055 | 0.844 | 0.709-1.004 |
| rs1997623/CC Reference | | | |
| CA Genotype | 0.001 | 1.569 | 1.209-2.1037 |
| AA Genotype | 0.538 | 0.778 | 0.350-1.729 |
| CA + AA Genotypes | 0.002 | 1.489 | 1.157-1.916 |

Example 2

In Silico Alignment

Figure 4:
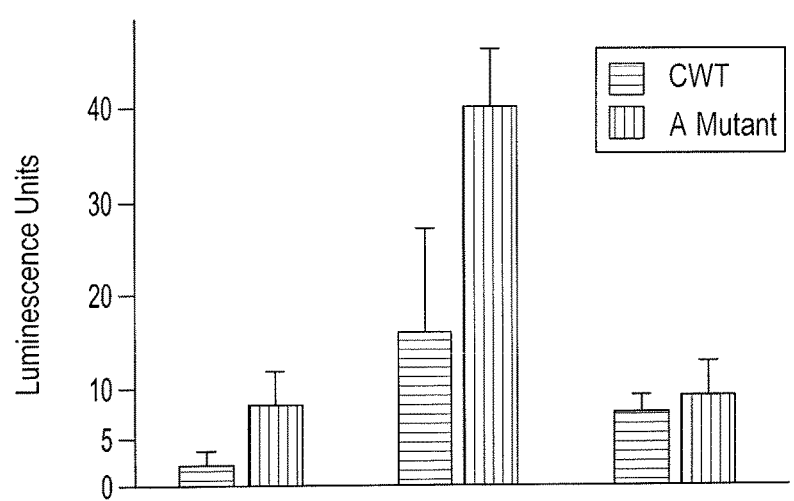
FIG. 4 depicts a bar graph of the effect of the CAV1 rs1997623 variant on caveolin-1 expression in human preadipocytes.
Figure 5:
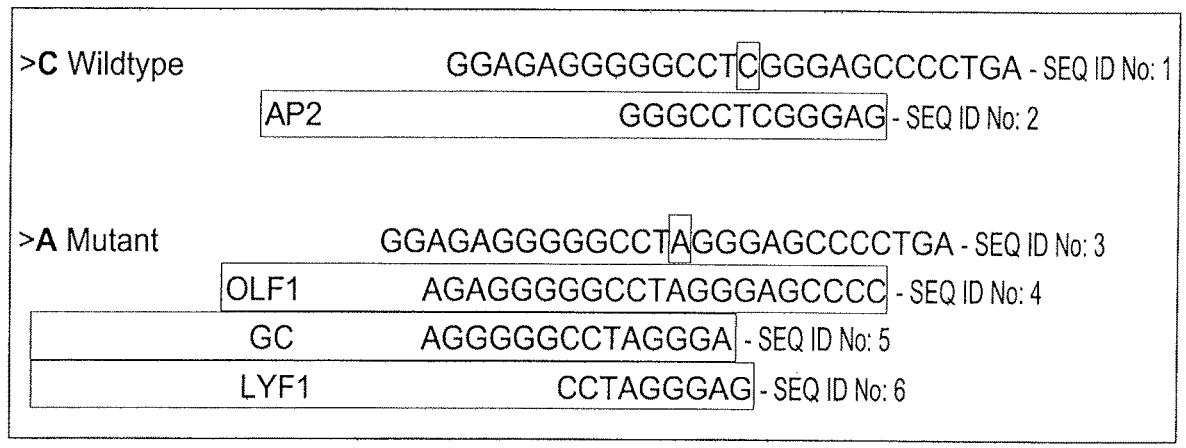
FIG. 5 depicts an alignment of predicted transcription factor binding sites to the CAV1 rs1997623 wild type and mutant sequences.
Figure 6A:
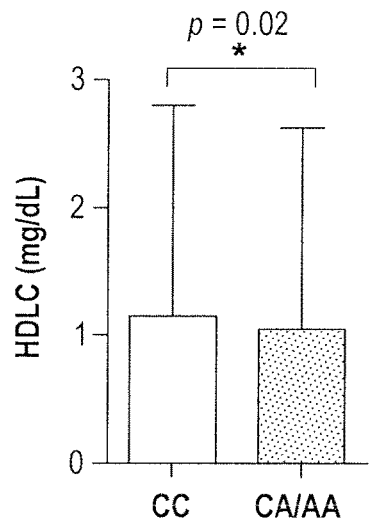
FIG. 6A depicts a bar graph of HDLC levels in participants with the CAV1 rs1997623 mutant and wild type alleles.
Figure 6B:
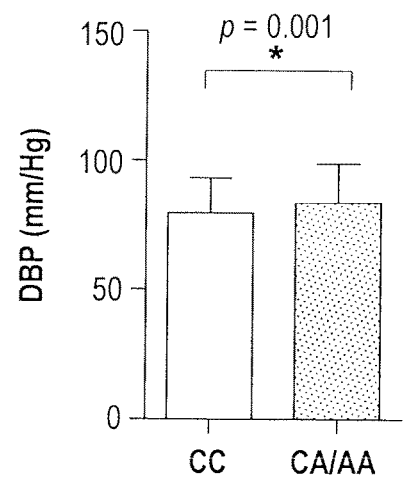
FIG. 6B depicts a bar graph of the diastolic blood pressure in participants with the CAV1 rs1997623 mutant and wild type alleles.
Figure 6C:
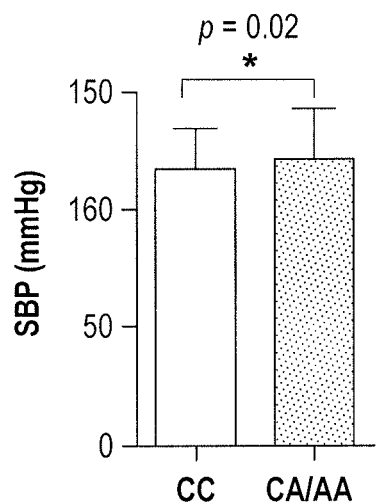
FIG. 6C depicts a bar graph of the systolic blood pressure in participants with the CAV1 rs1997623 mutant and wild type alleles.
Figure 6D:
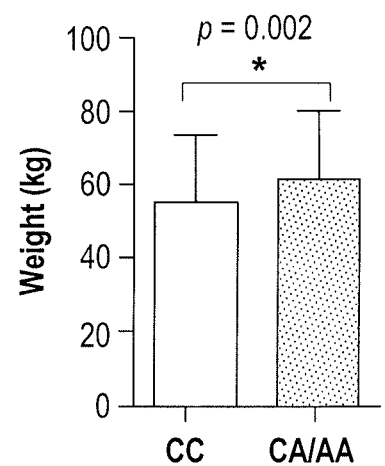
FIG. 6D depicts a bar graph of the weight of participants with the CAV1 rs1997623 mutant and wild type alleles.
Figure 6E:
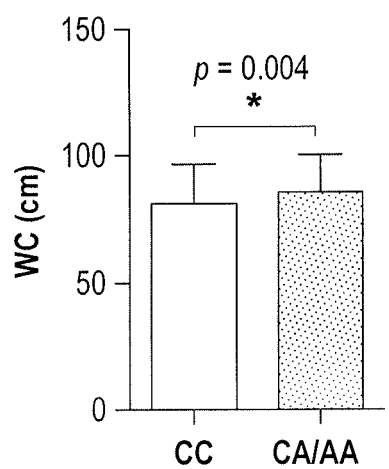
FIG. 6E depicts a bar graph of the waist circumference of participants with the CAV1 rs1997623 mutant and wild type alleles.
Figure 6F:
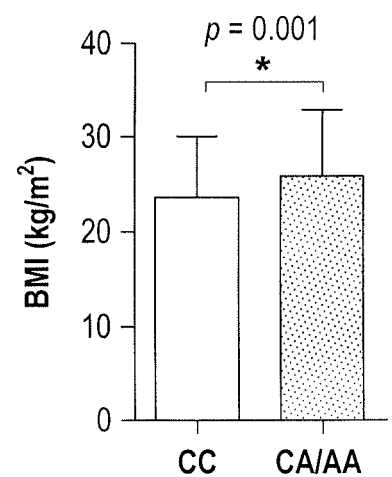
FIG. 6F depicts a bar graph of the BMI of participants with the CAV1 rs1997623 mutant and wild type alleles.

An in silico analysis was performed to predict the effect of the CAV1 rs1997623 SNP on the transcription factor binding sites for the CAV1 gene. The analysis identified three new transcription factors that might bind to the CAV1 rs1997623 SNP as compared to a single transcription factor that would bind to the CAV1 wild type genetic sequence, suggesting that the CAV1 rs1997623 SNP results in increased expression of the CAV1 gene (See FIG. 5). This prediction was further supported by a gene expression experiment, which found that the expression of caveolin-1 was significantly increased in human adipocytes having the CAV1 rs1997623 SNP when compared to caveolin-1 expression in wild type adipocytes (See FIG. 4).

It is to be understood that the method for determining predisposition to metabolic syndrome is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for preventing progression to metabolic syndrome in a human subject comprising:
   collecting a biological sample from the subject;
   detecting the subject's genotype at the CAV1 rs1997623 locus;
   detecting the presence of a CA at rs1997623 CAV1 risk variant in the biological sample;
   determining the subject with CA at rs1997623 is at increased risk for developing metabolic syndrome;
   and administering a pharmaceutical to the subject in need thereof, to prevent the subject from developing metabolic syndrome.

2. The method for preventing progression to metabolic syndrome of claim 1, wherein the pharmaceutical is selected from the group consisting of 18a-Glycyrrhetinic acid, Incadronate (disodium cycloleptylaminomethylene diphosphonate), Interleukin-4, a combination of Celecoxib and Lovastatin, an anti-CAV1 siRNA, and combinations thereof.

3. The method for preventing progression to metabolic syndrome of claim 1, wherein the subject is a child.

4. The method for preventing progression to metabolic syndrome of claim 1, wherein the biological sample is a non-invasive sample.

5. The method for preventing progression to metabolic syndrome of claim 3, wherein the biological sample is saliva.

* * * * *

SEQUENCE LISTING

<160> NUMBER OF SEQ ID NOS: 6

<210> SEQ ID NO 1
<211> LENGTH: 26
<212> TYPE: DNA
<213> ORGANISM: Homo sapiens

<400> SEQUENCE: 1
ggagaggggg cctcgggagc ccctga                                    26

<210> SEQ ID NO 2

```
<211> LENGTH: 12
<212> TYPE: DNA
<213> ORGANISM: Homo sapiens

<400> SEQUENCE: 2
gggcctcggg ag                                                          12

<210> SEQ ID NO 3
<211> LENGTH: 26
<212> TYPE: DNA
<213> ORGANISM: Homo sapiens

<400> SEQUENCE: 3
ggagaggggg cctagggagc ccctga                                           26

<210> SEQ ID NO 4
<211> LENGTH: 21
<212> TYPE: DNA
<213> ORGANISM: Homo sapiens

<400> SEQUENCE: 4 agaggggcc tagggagccc c                                                 21

<210> SEQ ID NO 5
<211> LENGTH: 14
<212> TYPE: DNA
<213> ORGANISM: Homo sapiens

<400> SEQUENCE: 5 aggggggccta ggga                                                       14

<210> SEQ ID NO 6
<211> LENGTH: 9
<212> TYPE: DNA
<213> ORGANISM: Homo sapiens

<400> SEQUENCE: 6 cctagggag                                                               9
```